United States Patent
Shaldon et al.

(10) Patent No.: US 6,284,141 B1
(45) Date of Patent: Sep. 4, 2001

(54) METHOD AND SYSTEM FOR PREVENTING INTRADIALYTIC SYMPTOMATOLOGY

(75) Inventors: Stanley Shaldon; Céline Granolleras, both of Montpellier (FR)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 09/308,969

(22) PCT Filed: Nov. 11, 1997

(86) PCT No.: PCT/SE97/01879

§ 371 Date: Aug. 4, 1999

§ 102(e) Date: Aug. 4, 1999

(87) PCT Pub. No.: WO98/23311

PCT Pub. Date: Jun. 4, 1998

(30) Foreign Application Priority Data

Nov. 28, 1996 (SE) .................................................. 9604370

(51) Int. Cl.[7] .................................................. B01D 61/32
(52) U.S. Cl. .......................... 210/739; 210/646; 210/647; 210/746; 210/85; 210/86; 210/97; 210/143; 210/321.65
(58) Field of Search .................................... 210/645, 646, 210/647, 739, 746, 85, 86, 97, 143, 321.65, 321.71, 650; 604/4.01, 5.01, 5.04

(56) References Cited

U.S. PATENT DOCUMENTS

| 4,469,593 | 9/1984 | Ishihara et al. ................... 210/96.2 |
| 4,722,798 | 2/1988 | Goss ..................................... 210/646 |
| 5,507,723 | * 4/1996 | Keshaviah ........................... 210/647 |
| 5,518,623 | * 5/1996 | Keshaviah et al. .................. 210/646 |
| 5,662,806 | * 9/1997 | Keshaviah et al. .................. 210/739 |
| 5,849,179 | * 12/1998 | Emerson et al. ..................... 210/87 |

FOREIGN PATENT DOCUMENTS

| 94/08641 | 4/1994 | (WO) . |
| 95/32010 | 11/1995 | (WO) . |
| 96/04401 | 2/1996 | (WO) . |

OTHER PUBLICATIONS

Patent Abstracts of Japan, vol. 13, No. 124, abstract of JP 63–294866 A (Iryo Kogaku Kenkyusho k.k.), Jan. 12, 1988.

* cited by examiner

Primary Examiner—John Kim
(74) Attorney, Agent, or Firm—Lerner, David, Littenberg, Krumholz & Mentlik, LLP (57) ABSTRACT

Methods and apparatus are disclosed for conducting blood treatment procedures. The method includes conducting the treatment procedure such as dialysis at a first efficiency until a limit value is reached, and then altering the first efficiency to a second efficiency until a second limit value has been reached. The method also includes devising a predetermined efficiency profile for the blood treatment procedure, conducting the procedure at a predetermined efficiency until a first limit value is reached, and then altering the efficiency of the blood treatment procedure in accordance with the predetermined efficiency profile.

22 Claims, 7 Drawing Sheets

Fig.7

METHOD AND SYSTEM FOR PREVENTING INTRADIALYTIC SYMPTOMATOLOGY

FIELD OF THE INVENTION

The present invention relates to the field of preventing intradialytic symptomatology during dialysis, such as hemodialysis, hemodiafiltration or hemofiltration, including both continuous and acute therapy.

BACKGROUND OF THE INVENTION

One intradialytic symptom is the disequilibrium syndrome which was first described in 1961. The disequilibrium syndrome is a set of systemic and neurologic symptoms that can occur either during or soon after dialysis. Early symptoms are nausea, vomiting, restlessness and headache, followed by seizures, obtundation and coma. Some believe that the cause is related to an acute increase in brain water content, while others believe that the cause relates to acute changes in the pH of the cerebrospinal fluid during dialysis. This problem is exacerbated when acute patients with very high plasma urea nitrogen values are subject to a dialysis which is too efficient.

The treatment for mild symptoms is to decrease the efficiency of the solute removal and pH changes, such as by reducing the blood flow. Hypertonic NaCl or glucose can also be administered.

With more severe symptoms, the dialysis session should be stopped. Intravenous mannitol may also be of benefit.

The disequilibrium syndrome can be avoided by using high NaCl concentrations of at least 140 mmol/l and by using glucose concentrations of at least 200 mg/dl. Decreasing the sodium dialysis solution during dialysis treatment has also been suggested.

Another common intradialytic complication is symptomatic hypotension, which is normally related to an excessively rapid decrease in the blood volume during dialysis. Today most dialysis machines use a volume control for ultrafiltration, which is a method which aids in preventing symptomatic hypotension. Other methods include the profiling of sodium, use of low temperature, switching from acetate to bicarbonate, etc.

Furthermore, ultrafiltration below the patient's dry weight may result in symptomatic hypotension associated with, for instance, cramps, dizziness, malaise and a washed-out feeling.

An object of the present invention is to solve these and related intradialytic complications during dialysis.

Biofeedback is a subject which is being investigated by many researchers. One example is U.S. Pat. No. 4,469,593 which discloses a blood purification apparatus including a hematocrit measurement apparatus. The hematocrit value is used for controlling a negative ultrafiltration pressure on the dialysate side of a dialyzer for maintaining the hematocrit value constant or according to a pre-defined profile. Also the conductivity of the blood or plasma is used in order to establish an upper limit for sodium, while the hematocrit value controls both the addition of replacement fluid and for increasing the sodium concentration in a hemofiltration apparatus. Finally, the oncotic pressure is also used for biofeedback.

International Patent No. WO 94/08641 discloses an on-line real time urea sensor which is used to measure the urea concentration in the effluent from a dialyzer. The system establishes two exponential fits of the urea concentration, with an early fit during the first 30 minutes and a late fit during the flowing treatment time. By obtaining an initial BUN-value, the Kt/V or SRI (solute removal index) can be calculated and projected to the intended time. In this way, the efficiency of the treatment can be measured on line. It is stated that the efficiency decreases at all times during the treatment time, although presumably more slowly at the end. It is also stated that deviation from a projected Kt/V value can be used for troubleshooting.

International Patent No. WO 95/32010 discloses a method of determining the optimum blood flow (as measured by pump speed) in order to obtain the most efficient dialysis. It is observed that the efficiency or clearance of the dialyzer is dependent on the blood flow rate (and dialysis flow rate, as well as temperature, etc.). However, above a predetermined blood flow, the efficiency of the dialyzer once again decreases. There are several factors for this phenomenon, one of which is fistula recirculation. According to International Patent No. WO 95/32010, the efficiency of the dialyzer is determined at different blood flows, for example in increments of 50 ml/min, and the blood flow at maximum clearance is used. The maximum blood flow is determined at the start of each treatment. If this maximum blood flow declines after a number of weeks or days, it can be a sign of fistula malfunction. In this specification, a urea sensor is used for assessing the efficiency of the treatment at the start.

SUMMARY OF THE INVENTION

An object of the present invention is to provide a method and apparatus for performing dialysis or a similar treatment as fast as possible, while minimizing the inconvenience to the patient.

It has now been found that each patient has a characteristic curve for maximum tolerated treatment efficiency versus time. According to the present invention, the treatment is performed as efficiently as possible until that curve is reached or approached, and thereafter the treatment efficiency is decreased so that the curve is never reached.

In an alternative embodiment of the present invention, the dialysis treatment is preceded by isolated ultrafiltration. The dialysis treatment is performed with high efficiency until the characteristic curve is approached. The continued treatment is then performed with decreasing efficiency so that the curve is never reached.

In accordance with the present invention, these and other objects have now been accomplished by the discovery of a method of conducting a blood treatment procedure comprising conducting the blood treatment procedure at a first predetermined efficiency until a first predetermined limit value has been reached, and altering the first predetermined efficiency to a second predetermined efficiency until a second predetermined limit value has been reached. Preferably the second predetermined efficiency comprises a predetermined efficiency profile including at least a third predetermined efficiency.

In accordance with one embodiment of the method of the present invention, the method includes terminating the method upon reaching the second predetermined limit value.

In accordance with another embodiment of the method of the present invention, the first predetermined efficiency comprises a higher efficiency than the second predetermined efficiency.

In accordance with a preferred embodiment of the method of the present invention, the blood treatment procedure comprises dialysis. Preferably the second predetermined limit value comprises a predetermined dialysis dosage.

In accordance with the present invention, a method has been discovered for conducting a blood treatment procedure comprising devising a predetermined profile of efficiency for the blood treatment procedure, conducting the blood treatment procedure at a predetermined efficiency until a first predetermined limit value has been reached, and altering the efficiency of the blood treatment procedure in accordance with the predetermined profile of efficiency. Preferably the blood treatment procedure comprises dialysis.

In accordance with one embodiment of the method of the present invention, the method includes devising a characteristic curve of efficiency for a specific patient and determining the first predetermined limit value based upon reaching the characteristic curve. Preferably the method includes measuring the amount of urea removed by the dialysis and determining the first predetermined limit value based upon removal of a predetermined amount of the urea. In a preferred embodiment, the method includes determining a urea generation rate for a specific patient and the predetermined amount of the urea is based upon the urea generation rate.

In accordance with a preferred embodiment of the method of the present invention, the method includes determining the predetermined amount of urea based upon the product of the urea generation rate, the time between the dialysis procedure and a second dialysis procedure, and a predetermined patient factor.

In accordance with another embodiment of the method of the present invention, the method includes measuring the concentration of urea removed by the dialysis, and determining the first predetermined limit value based upon a predetermined concentration of the urea.

In accordance with another embodiment of the method of the present invention, the determining of the profile of efficiency for the blood treatment procedure comprises altering the flow of blood or the flow of a dialysis fluid through a dialyzer. Preferably, the method includes devising a characteristic curve of efficiency for a specific patient, wherein the determining of the profile of the efficiency for the blood treatment procedure is based upon a curve approaching the characteristic curve. In a preferred embodiment, the determining of the profile of the efficiency is carried out stepwise or continuously.

In accordance with a preferred embodiment of the method of the present invention, the predetermined profile of the efficiency is based upon the urea concentration of the dialysis outlet fluid, and the determining of the profile of the efficiency for the dialysis is based upon maintaining the urea concentration upon the predetermined profile.

In accordance with the present invention, apparatus has been discovered for conducting a blood treatment procedure comprising means for conducting the blood treatment procedure at a first predetermined efficiency until a first predetermined limit value has been reached and means for altering the first predetermined efficiency to a second predetermined efficiency until a second predetermined limit value has been reached. Preferably, the apparatus includes means for terminating the blood treatment procedure upon reaching the second predetermined limit value.

In accordance with the present invention, apparatus has been provided for conducting a blood treatment procedure comprising means for determining a predetermined profile of efficiency for the blood treatment procedure, means for conducting the blood treatment procedure at a first predetermined efficiency until a first predetermined limit value has been reached, and means for altering the efficiency of the blood treatment procedure in accordance with the predetermined profile of efficiency. Preferably the blood treatment procedure comprises dialysis.

In accordance with one embodiment of the apparatus of the present invention, the apparatus includes means for devising a characteristic curve of efficiency for a specific patient and means for determining the first predetermined limit value upon reaching the characteristic curve.

In accordance with another embodiment of the apparatus of the present invention, the apparatus includes means for measuring the amount of urea removed by the dialysis, and means for determining the first predetermined limit value based upon the predetermined amount of the urea removed. In a preferred embodiment, the apparatus includes means for determining a urea generation rate for a specific patient and means for determining the predetermined amount of urea removed based upon the urea generation rate. Preferably the apparatus includes means for determining the predetermined amount of the urea removed based upon the product of the urea generation rate, the time between the dialysis and a second dialysis procedure, and a predetermined patient factor.

In accordance with another embodiment of the apparatus of the present invention, the apparatus includes means for measuring the concentration of urea removed by the dialysis, and means for determining the first predetermined limit value based upon a predetermined concentration of the urea.

In accordance with another embodiment of the apparatus of the present invention, the means for determining the profile of efficiency for the blood treatment procedure comprises means for altering the flow of blood or the flow of dialysis fluid through a dialyzer. Preferably the apparatus includes means for devising a characteristic curve of efficiency for a specific patient, wherein the means for determining of the profile of the efficiency for the treatment procedure is based upon a curve approaching the characteristic curve. In a preferred embodiment, the means for determining the profile of the efficiency is carried out stepwise or continuously.

In accordance with another embodiment of the apparatus of the present invention, the apparatus includes means for determining a predetermined profile, and wherein the means for determining the profile of the efficiency for the blood treatment procedure is based upon the urea concentration of the dialysis outlet fluid.

In accordance with another embodiment of the apparatus of the present invention, the blood treatment procedure is hemodialysis, hemofiltration and hemodiafiltration.

BRIEF DESCRIPTION OF THE DRAWINGS

The PRESENT invention will be described in more detail with reference to the following detailed description, which in turn refers to the drawings wherein.

DETAILED DESCRIPTION

According to the present invention, it has been found that a specific patient being exposed to efficient dialysis, for example with the target of Kt/V being equal to 2.0 or higher, will risk becoming symptomatic if the efficiency is too high and the dialysis time is too short. For example, a patient prescribed at Kt/V=2.0 during 4 hours will require an efficiency of K/V=0.5, which could result in the collapse of this patient. However, if the time was increased to 5 hours and, consequently, the efficiency was decreased to K/V=0.4, then the patient could stand the treatment without collapse or reaching his breakpoint. Other patients may become symptomatic even at lower Kt/V values and the efficiencies in the above figures are only given as an example.

Figure 1:
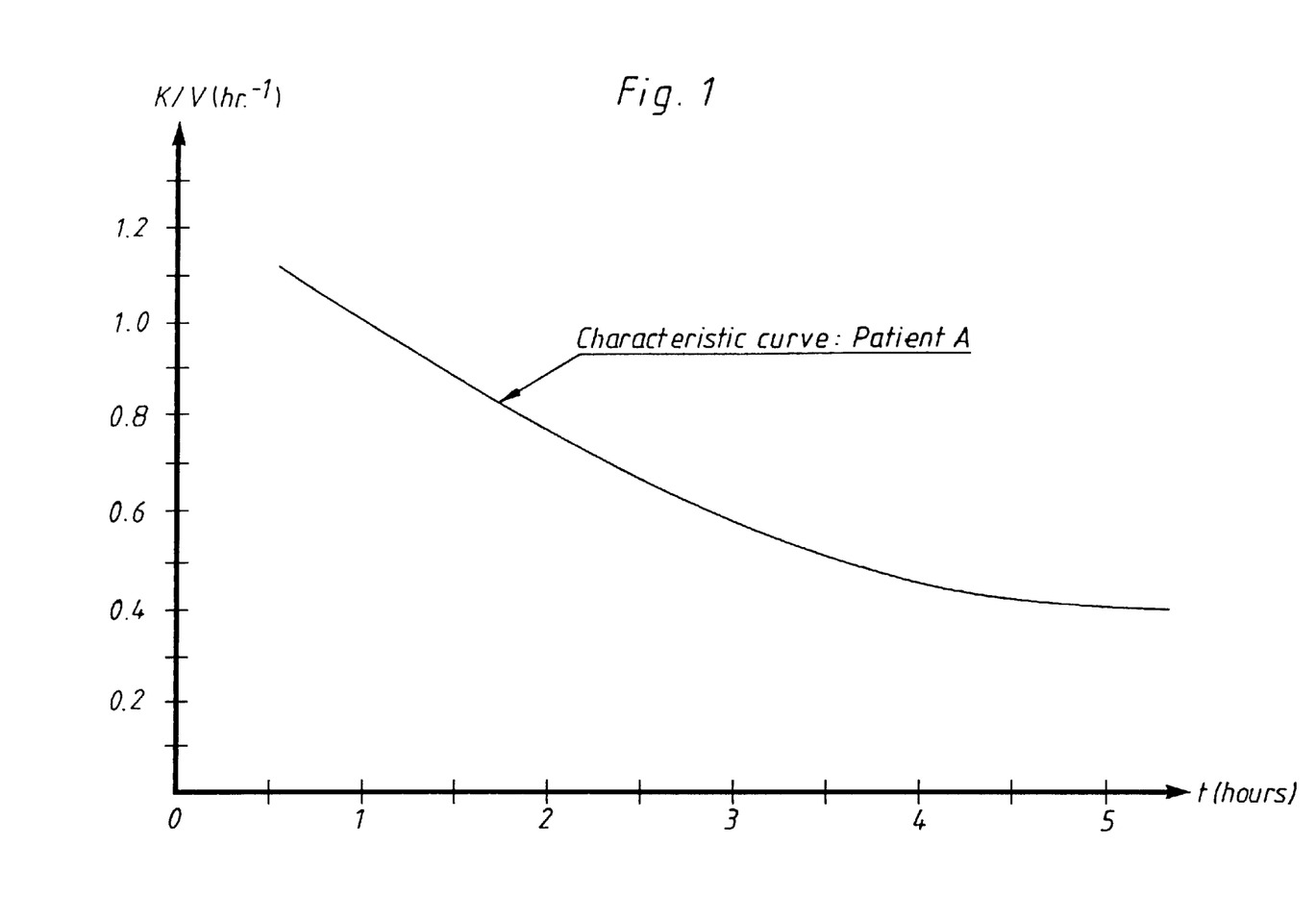
FIG. 1 is a graphical representation of a typical characteristic curve for a specific patient.

It has now been found that a specific patient has a characteristic curve as shown in FIG. 1. If the curve is exceeded, the patient will break down. As can be seen from FIG. 1, it would not be possible to reach the goal of Kt/V=2.0 in 4 hours without passing the characteristic curve.

It is probable that the characteristic curve is in fact a series of curves depending on other factors of the dialysis, such as ultrafiltration rate, start BUN, sodium concentration or profiling, bicarbonate concentration, as well as psychological or physiological factors, such as illness or depression, etc.

According to the present invention, the efficiency of the treatment is profiled according to a specific profile adapted to the patient. Such a profile could involve starting with as high efficiency as possible, for example K/V=0.6 during one hour, then decreasing the efficiency stepwise to K/V=0.5 during the second hour, K/V=0.4 during the third hour and K/V=0.3 during the last hour, which would result in a Kt/V value of 1.8 during four hours. By on line measurement of the efficiency using a urea monitor, the process can be monitored so that the desired efficiency is obtained in reality, and the efficiency can be adjusted automatically to follow the desired profile.

In a preferred embodiment, the efficiency of the treatment is as high as possible at the start, until a limit value is reached, which is indicative of the fact that the patient is approaching his characteristic curve and can no longer withstand high efficiency dialysis. After the limit value has been reached, the efficiency is then changed according to a predetermined curve. When the desired goal has been obtained, the treatment is terminated.

The limit value can be determined in several ways. It can be determined empirically so that the characteristic curve of a specific patient is determined by exposing him to different dialysis efficiencies and monitoring specific patient data. In this manner, the limit value can be established by looking into the curve.

It is often not possible to expose a specific patient to such different dialysis efficiencies, and to drive the patient to disequilibrium conditions merely in order to obtain a characteristic curve.

Another approach is to monitor the removal of urea by the urea monitor, and when a predetermined amount of urea has been removed, the limit value has been reached.

This amount of urea is obtained by integrating the values obtained by the urea sensor, which are concentration values. If it can be assumed that the dialysis fluid flow is constant, the total removed urea (TRU) is the integral of the concentration curve. Otherwise, the concentration curve can be multiplied by the volume flow of the dialysis fluid at any time and then integrated to obtain the mass of urea removed.

The amount of urea can be a predetermined proportion of the urea production between the dialysis sessions, for example, between about 50% and 90%, or preferably between about 65% and 80%, for example, about 75%, of the urea generated between the dialysis treatments. Often it can be assumed that the urea generation is fairly constant during a short time span, such as a week. Formulae are known for the urea generation for hemodialysis patients, which can be used for initial determination of this amount of urea removed for reaching the disequilibrium limit value.

Another approach to determining when the patient is close to his characteristic curve would be to monitor when the concentration in the blood reaches a predetermined lower value, which is indicative of reaching that limit value. It is more convenient to monitor the concentration in the dialysis fluid, which, however, is a mirror of the concentration in the blood.

After reaching the limit value, the efficiency is changed. One approach is to decrease the efficiency step-wise, for example in increments of from about 0.1 to about 0.01 for the efficiency K/V.

Figure 2:
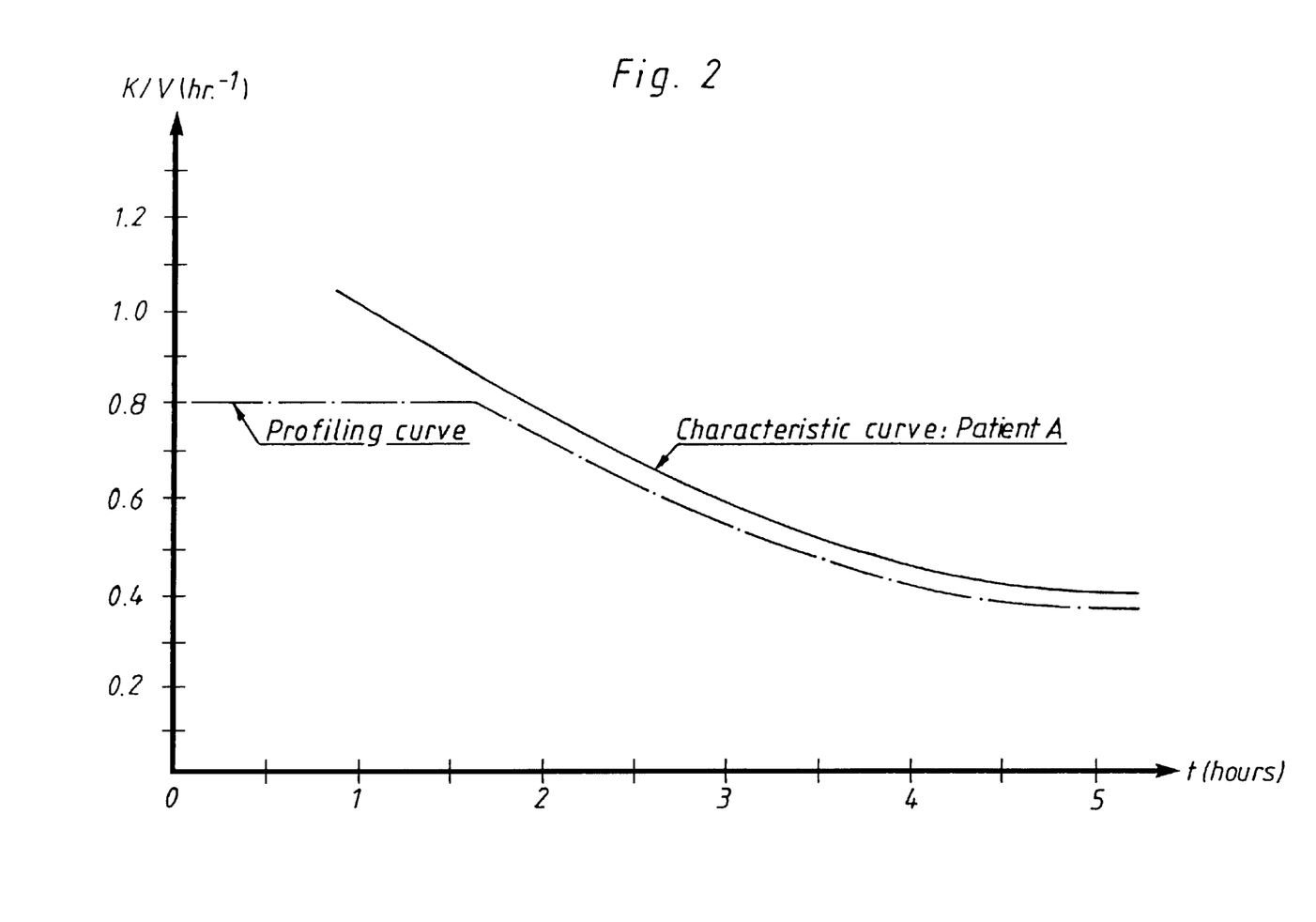
FIG. 2 is a graphical representation of an efficiency curve.

Another approach is to use an exponential declination of the efficiency, as is outlined in FIG. 2.

The urea monitor concentration values may be used for controlling the efficiency. From the start, the highest possible efficiency is allowed. When the concentration value at the urea monitor reaches a low value, indicative of approaching the characteristic curve, the efficiency is controlled or altered so that the urea monitor concentration value follows a predetermined curve, such as the efficiency curve of FIG. 2.

Consequently, the dialysis efficiency is adapted to the patient and to the concentration gradient he can withstand across the brain barrier without breaking down. In this case, the concentration gradient is dependent on the initial concentration of urea in the brain, which, however, is dependent on the urea generation rate between the dialysis sessions. If it is assumed that the urea generation rate is fairly constant, the predetermined low concentration value of the urea monitor can be calculated in relation to the urea generation rate.

It is believed that the reason for reaching a time limit is the fact that the urea in the body is distributed between different compartments, for example extracellular and intracellular compartments. Urea in the extracellular compartment is readily available for dialysis by the high-efficiency dialysis process. When the urea in the extracellular compartment has been rapidly removed, the urea concentration in the blood will be low. Consequently, there is a high concentration gradient over those membranes, which do not readily pass the urea molecule, such as the brain barrier. Such high gradients are known to trigger the disequilibrium syndrome. Moreover, such high gradients will cause water to pass the brain barrier in the opposite direction, increasing the intracranial pressure, which may also induce the disequilibrium syndrome.

If a higher efficiency is used from the start, the extracellular compartment will be depleted faster without allowing the intracellular compartment a sufficient time to give off any appreciable amount of urea. On the other hand, if a lower efficiency is used from the start, the patient can withstand the dialysis for longer time, since the intracellular compartment has time to contribute to the urea in the blood. This suggests why increased efficiency cannot be tolerated for a long period of time.

While this is a plausible explanation, we do not want to bind ourselves to this explanation, since there are many other factors contributing to the removal of urea. Moreover, urea is only one of the molecules removed during a dialysis session, and it cannot be ruled out that other molecules play an important role in the disequilibrium syndrome. Urea is commonly used as a marker molecule for dialysis efficiency.

The dialysis efficiency can be influenced in several ways. The most convenient way is to change the blood flow rate, which has a direct, although non-linear relationship to the efficiency. It is also possible to change the dialysis fluid flow rate, which gives approximately the same results. Or both the blood flow rate and dialysis flow rate may be altered. The same applies to hemofiltration and hemodiafiltration.

Figure 3:
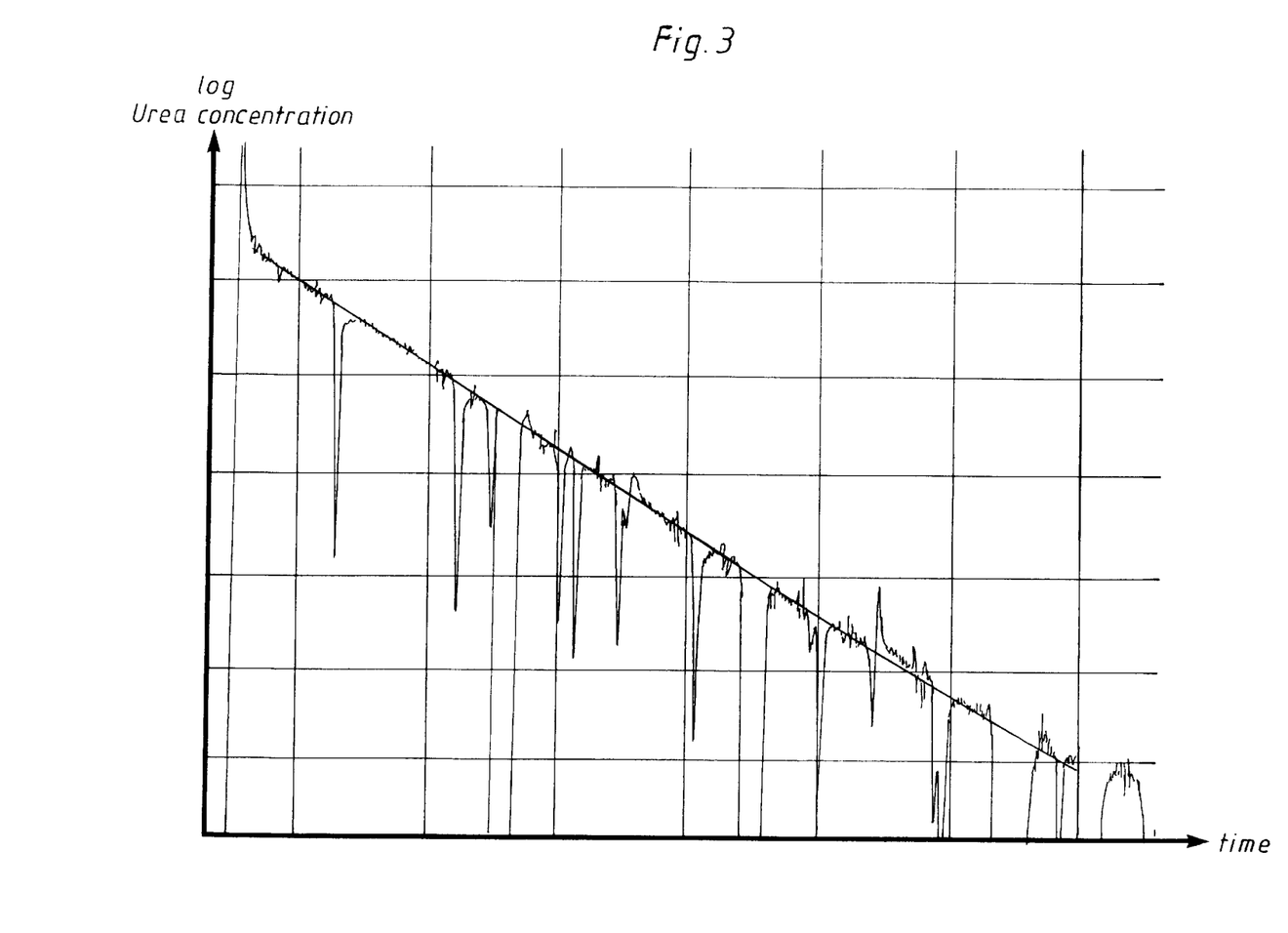
FIG. 3 is a graphical representation of a typical urea sensor output curve.

The dialysis efficiency is obtained by monitoring the urea concentration in the outgoing dialysis fluid flow. A typical urea concentration curve is shown in FIG. 3. The slope of the logarithm of the curve corresponds in principle to the efficiency, K/V.

Figure 4:
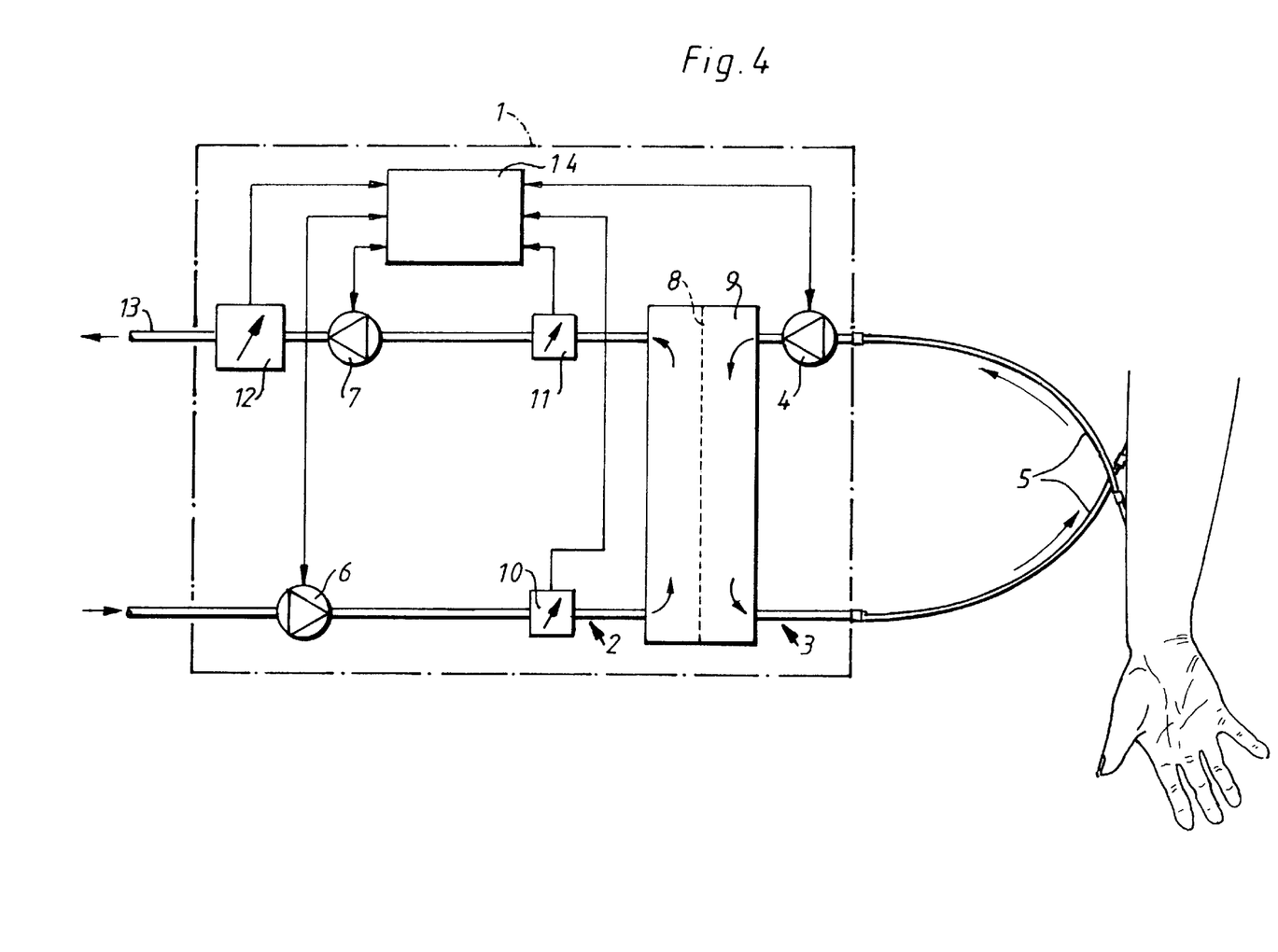
FIG. 4 is a schematic representation of a dialysis machine incorporating the present invention.

A typical dialysis machine is schematically shown in FIG. 4. The dialysis machine 1 comprises a dialysis fluid preparation portion 2 and a blood flow portion 3.

The blood flow portion 3 comprises a pump 4 which propels the blood in the extracorporeal blood circuit 5.

The dialysis fluid preparation portion 2 includes pumps, 6 and 7, which control the fluid flow rate of the dialysis fluid, as well as the ultrafiltration pressure applied across a membrane 8 of a dialyzer 9. Two fluid flow meters, 10 and 11, determine the dialysis fluid flow rate, as well as the ultrafiltration flow obtained from the blood.

A urea monitor 12 is included in an outlet line 13 from the dialysis machine. The urea monitor is disclosed in details in International Patent No. WO 96/04401, which is incorporated herein by reference thereto. The urea monitor 12 accurately determines the urea concentration in the outlet dialysis fluid line 13.

All signals from the flow meters, 10 and 11, pumps, 4, 6, and 7, and urea monitor 12 are fed to a computer 14.

The urea removal rate from blood is equal to the concentration times the dialysis fluid flow, since no urea is included in the incoming dialysis fluid. The total removed urea (TRU) is determined automatically by the urea monitor on a continuous basis.

When performing the method according to the present invention, the urea concentration values obtained by the urea monitor are used for determining the initial efficiency K/V of the dialyzer of the dialysis treatment. This requires that the urea monitor be connected for a sufficient period of time so that a sufficient amount of data has been collected. Usually, the efficiency is higher during the first 20 to 30 minutes and then declines to a more constant value. Consequently, it is often desired to wait for more than about 30 minutes before determining the initial or actual efficiency.

When the actual efficiency of a specific dialysis session has been established, it can be assumed that the efficiency is approximately constant if no other factors are altered. In reality, there is a small decrease in the efficiency over time, but it can be neglected for the purposes of the present explanation. Of course, the computer for the dialysis machine can be programmed to take account of such known variations.

After determining that the limit value has been reached by any of the above-mentioned methods, the computer 14 for the dialysis machine is programmed to change the efficiency, usually by decreasing it. The relationship between the blood flow and the efficiency for a specific dialyzer can be included in the memory of the computer 14, and the computer can be programmed to change the efficiency as required, for example stepwise or continuously according to an exponential curve.

The urea monitor is used for determining the new efficiency after each alteration, and the efficiency values are integrated over time to indicate when a desired dose (Kt/V) of dialysis has been reached, whereupon the dialysis session may be ended. Of course, other methods for determining when the dialysis session should be ended may be used, such as manual or time controlled ending.

The same profiling method can also be used for hemodiafiltration and hemofiltration.

Figure 5:
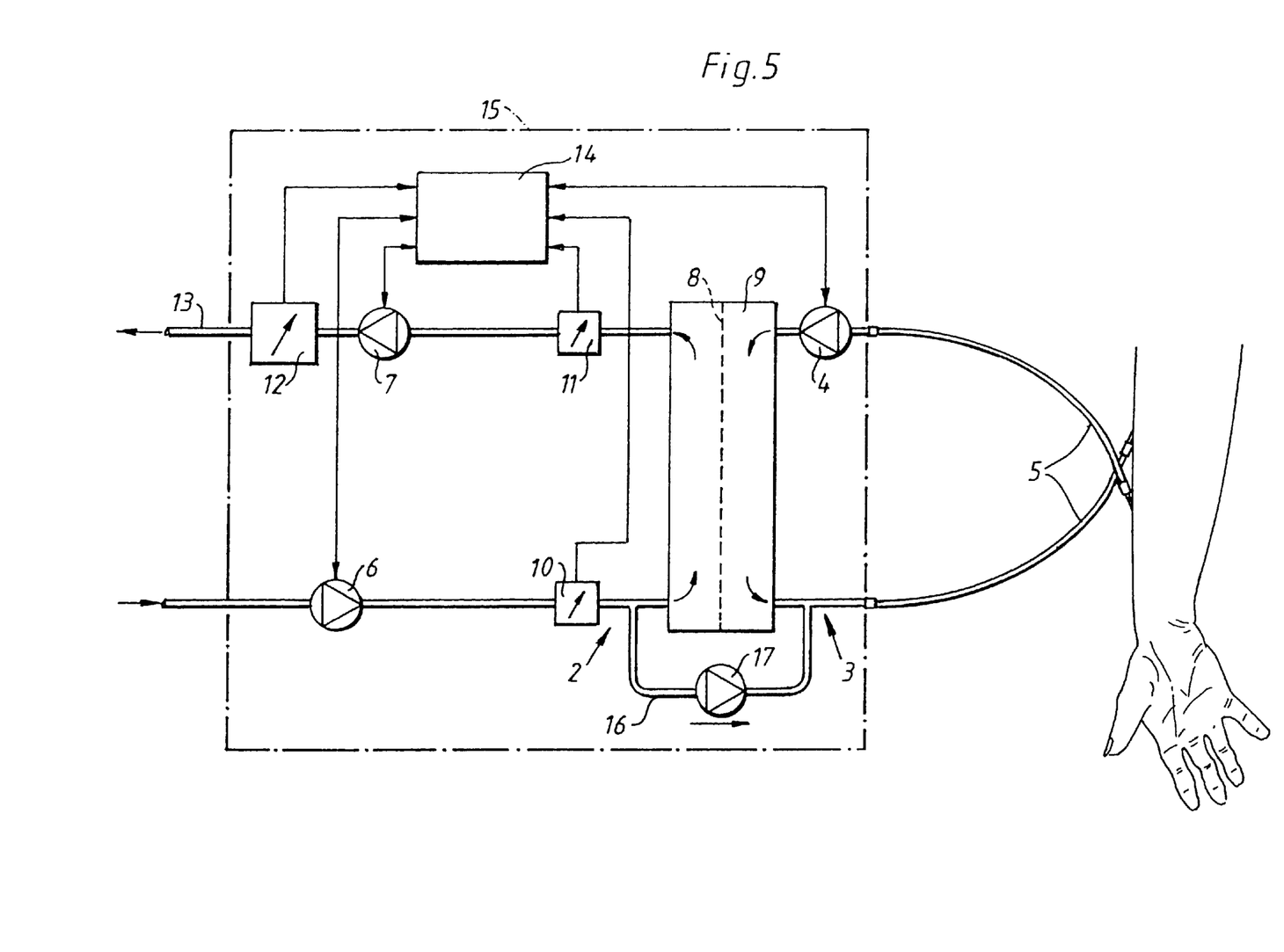
FIG. 5 is a schematic representation of a hemodiafiltration machine incorporating the present invention.

FIG. 5 shows an embodiment which is intended for hemodiafiltration. All components which are equal to the components of the hemodialysis machine 1 shown in FIG. 4 have the same reference numerals as in FIG. 4.

In order to obtain the hemodiafiltration machine 15 of FIG. 5, essentially only a line 16 is added to the hemodialysis machine of FIG. 4, connecting the outlet of flow meter 10 to the extracorporeal circuit 5 for introducing a replacement fluid into the patient. The line 16 also comprises a pump 17 for controlling the amount of replacement fluid introduced into the patient through the extracorporeal circuit 5. Of course, the replacement fluid should be sterile.

The amount of ultrafiltration is still controlled by the pumps, 6 and 7, as measured by flow meters, 10 and 11. The volume of replacement fluid introduced by pump 17 must be removed from the blood in the dialyzer, thereby increasing the filtration.

According to the present invention, the efficiency of the treatment should be varied, and usually decreased during the treatment. Such a decrease can be obtained by decreasing the blood flow in the hemodiafiltration machine 15 disclosed in FIG. 5. Another way of decreasing the efficiency would be to decrease the replacement fluid flow, until, ultimately, the treatment is converted to hemodialysis when the replacement fluid flow is zero.

Figure 6:
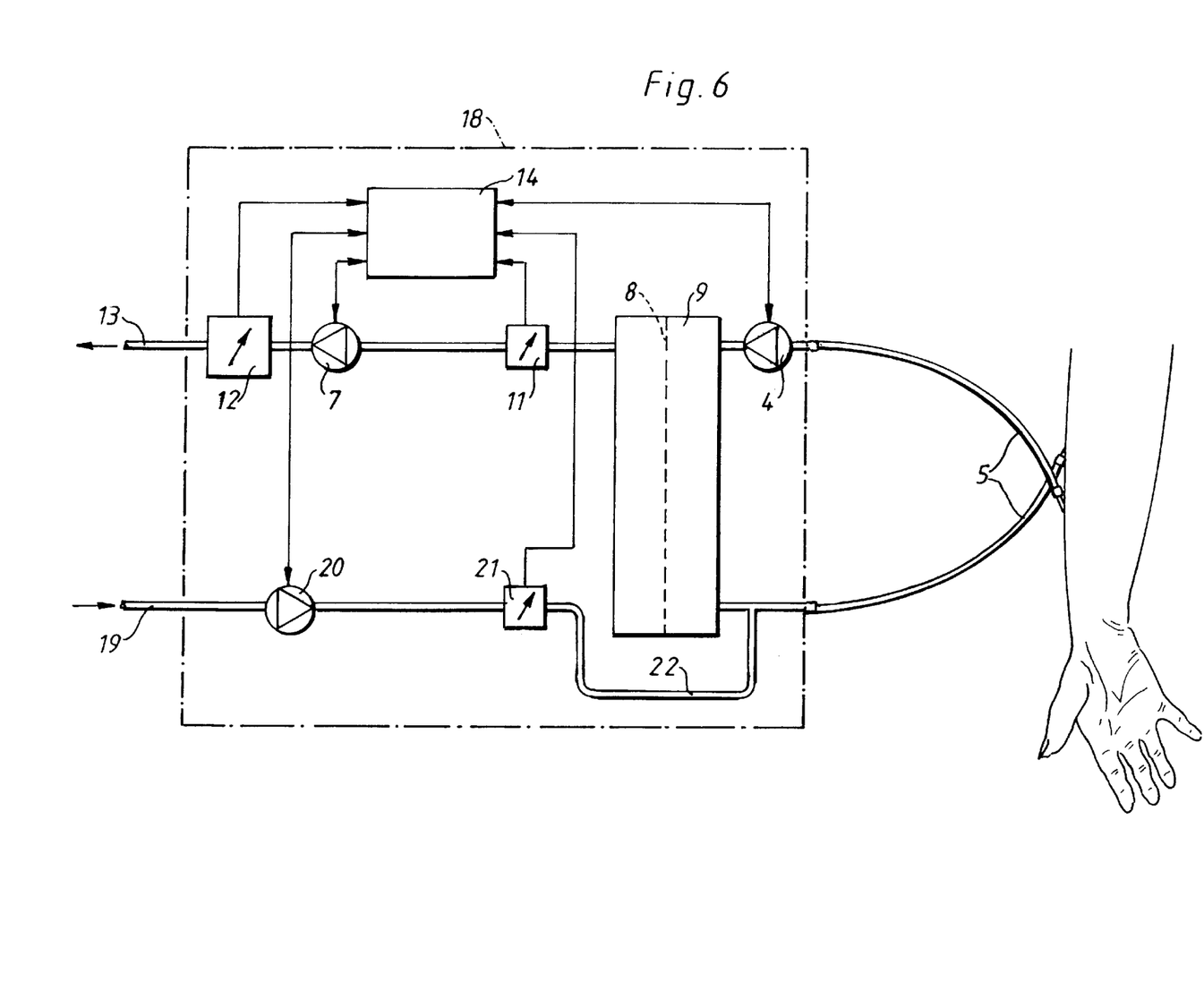
FIG. 6 is a schematic representation of a hemofiltration machine incorporating the present invention.

Another embodiment of the present invention is disclosed in FIG. 6, which shows a hemofiltration machine 18. Some of the components are the same as those in the embodiment of FIG. 4, and thus have the same reference numerals. However, the dialyzer 9 has no inlet line for dialysis fluid, but that line is replaced with a replacement fluid line 19 comprising a pump 20, a flow meter 21 and a line 22 for connection to the extracorporeal circuit 5 for introducing the replacement fluid into the blood of the patient. FIG. 6 shows postdilution, where the replacement fluid is introduced after the dialyzer, but also predilution may be used, where the replacement fluid is introduced into the extracorporeal circuit 5 before the dialyzer.

According to the present invention, the efficiency of the treatment is varied or decreased by decreasing the replacement fluid flow and/or the blood flow. The ultrafiltration is maintained constant by the machine by means of the computer 14 calculating the difference between the flow meters, 11 and 21, and controlling the pumps, 7 and 20, in dependence of the measured values.

Figure 7:
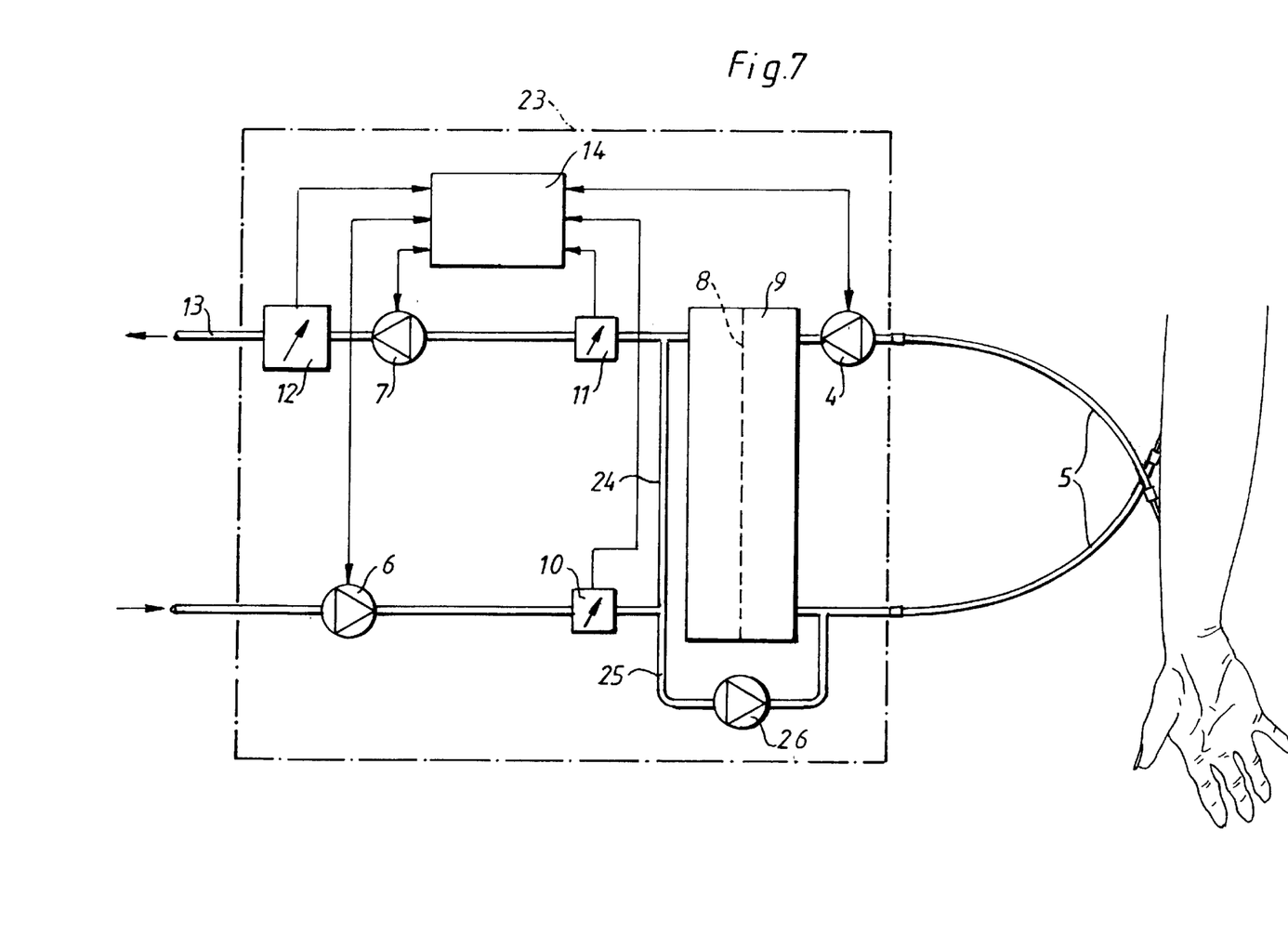
FIG. 7 is a schematic representation of another hemofiltration machine incorporating the present invention.

Another embodiment of a hemofiltration machine 23 is shown in FIG. 7. A portion of the inlet dialysis fluid is transferred to the outlet line 13 through a short-circuit line 24. Another portion of the dialysis fluid is taken out through line 25 to form a replacement fluid metered by means of a pump 26. The portions are known to computer 14 via flow meters, 10 and 11, and the speed of pump 26.

According to the present invention, the efficiency of the treatment is varied or decreased by decreasing the speed of pump 26 and/or decreasing the speed of pump 4.

As indicated above, other factors influence the dialysis treatment, and specifically water removal or ultrafiltration. A high ultrafiltration can result in intradialytic symptoms, most commonly symptomatic hypotension. However, it has been found that profiling of the efficiency will also improve the patient's resistance against symptomatic hypotension induced by high ultrafiltration during hemodialysis or hemofiltration.

Certain embodiments of the present invention have been described herein. It is clear to the skilled person that the present invention can be modified and adapted to different dialysis machines and urea monitors within the scope of the invention. For example, other marker molecules than urea, such as creatinine, can be used for the purpose of this invention, whereby the urea monitor is replaced by a creatinine monitor. The invention can also be adapted to peritoneal dialysis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of conducting a blood treatment procedure comprising conducting said blood treatment procedure at a first predetermined efficiency and before reaching a first predetermined time limit value, said time limit value being determined on the basis of a patient specific parameter, altering said first predetermined efficiency to a second predetermined efficiency wherein said first predetermined efficiency is higher than said second predetermined efficiency, and wherein said blood treatment procedure is selected from the group consisting of hemodialysis, hemofiltration and hemodiafiltration.

2. The method of claim 1 wherein said second predetermined efficiency comprises a predetermined efficiency profile including at least a third predetermined efficiency.

3. The method of claim 1 wherein said first predetermined time limit value is the time when a predetermined dialysis dose has been reached, said dialysis dose being a function of said first predetermined efficiency.

4. A method of conducting a blood treatment procedure comprising devising a predetermined profile of efficiency based on a patient specific characteristic curve for said blood treatment procedure, conducting said blood treatment procedure at a first predetermined efficiency, and before reaching a first predetermined time limit value determined on the basis of said characteristic curve altering said efficiency of said blood treatment procedure in accordance with said predetermined profile of efficiency wherein said altered efficiency is lower than said first predetermined efficiency, and wherein said blood treatment procedure is selected from the group consisting of hemodialysis, hemofiltration and hemodiafiltration.

5. The method of claim 4 including measuring an amount of urea removed by said dialysis and determining said first predetermined time limit value based upon removal of a predetermined amount of said urea.

6. The method of claim 5 including determining a urea generation rate for a specific patient and wherein said predetermined amount of urea is based upon said urea generation rate.

7. The method of claim 6 including determining said predetermined amount of urea based upon the product of said urea generation rate, the time between said dialysis procedure and a second dialysis procedure, and a predetermined patient factor.

8. The method of claim 4 including measuring the concentration of urea removed by said dialysis in the dialysis outlet fluid, and determining said first predetermined time limit value based upon a predetermined concentration of said urea.

9. The method of claim 4 wherein said determining of said profile of efficiency for said blood treatment procedure comprises altering at least one of blood flow rate and a dialysis fluid flow rate through a dialyzer.

10. The method of claim 9 including devising a characteristic curve of efficiency for a specific patient, wherein said determining of said profile of said efficiency for said blood treatment procedure is based upon a curve approaching said characteristic curve.

11. The method of claim 10 wherein said determining of said profile of said efficiency is carried out stepwise or continuously.

12. The method of claim 11 wherein said predetermined profile of said efficiency is based upon the urea concentration of said dialysis fluid through said dialyzer, and wherein said determining of said profile of efficiency for said blood treatment procedure is based upon maintaining said urea concentration upon said predetermined profile.

13. Apparatus for conducting a blood treatment procedure comprising means for conducting said blood treatment procedure at a first predetermined efficiency, and means for altering said first predetermined efficiency to a second, lower, predetermined efficiency before reaching a first predetermined time limit value wherein said predetermined time limit value is determined on the basis of a patient specific parameter, and wherein said blood treatment procedure is selected from the group consisting of hemodialysis, hemofiltration and hemodiafiltration.

14. Apparatus for conducting a blood treatment procedure comprising means for devising a predetermined profile of efficiency based on a patient specific characteristic curve for said blood treatment procedure, means for conducting said blood treatment procedure at a first predetermined efficiency, and means for altering said efficiency of said blood treatment procedure in accordance with said predetermined profile of efficiency, before reaching a first predetermined time limit value, wherein said first predetermined time limit value is determined on the basis of a patient specific parameter, and wherein said blood treatment procedure is selected from the group consisting of hemodialysis, hemofiltration and hemodiafiltration.

15. The apparatus of claim 14 including means for measuring an amount of urea removed by said dialysis, and means for determining said first predetermined time limit value based upon a predetermined amount of said urea removed.

16. The apparatus of claim 15 including means for determining a urea generation rate for a specific patient and means for determining said predetermined amount of urea removed based upon said urea generation rate.

17. The apparatus of claim 16 including means for determining said predetermined amount of said urea removed based upon the product of said urea generation rate, the time between said dialysis and a second dialysis procedure, and a predetermined patient factor.

18. The apparatus of claim 14 including means for measuring the concentration of urea removed by said dialysis, and means for determining said first predetermined limit value based upon a predetermined concentration of said urea.

19. The apparatus of claim 14 wherein said means for determining said profile of efficiency for said blood treatment procedure comprises means for altering at least one of blood flow rate and a dialysis fluid flow rate through a dialyzer.

20. The apparatus of claim 19 including means for devising a characteristic curve of efficiency for a specific patient, wherein said means for determining of said profile of said efficiency for said treatment procedure is based upon a curve approaching said characteristic curve.

21. The apparatus of claim 20 wherein said means for determining said profile of said efficiency is carried out stepwise or continuously.

22. The apparatus of claim 19 including means for determining a predetermined profile, and wherein said means for determining the profile of said efficiency for said blood treatment procedure is based upon a urea concentration of said dialysis fluid through said dialyzer.

* * * * *

UNITED STATES PATENT AND TRADEMARK OFFICE
CERTIFICATE OF CORRECTION

PATENT NO. : 6,284,141 B1
DATED : September 4, 2001
INVENTOR(S) : Shaldon et al.

It is certified that error appears in the above-identified patent and that said Letters Patent is hereby corrected as shown below:

Title page,
Item [75], Inventors, after "Stanley Shaldon" insert -- Monaco, Monaco --; after "Granolleras" insert -- Nimes, France -- and delete "both of Montpellier (FR)".

Signed and Sealed this

Sixteenth Day of April, 2002

*Attest:*

*Attesting Officer*

JAMES E. ROGAN
*Director of the United States Patent and Trademark Office*